United States Patent [19]
Wilson et al.

[11] Patent Number: 5,246,845
[45] Date of Patent: Sep. 21, 1993

[54] HETEROSPECIFIC MODIFICATION AS A MEANS TO CLONE RESTRICTION GENES

[75] Inventors: Geoffrey G. Wilson, Boxford; Marta M. Meda, Beverly, both of Mass.

[73] Assignee: New England Biolabs, Inc., Beverly, Mass.

[21] Appl. No.: 967,409

[22] Filed: Oct. 27, 1992

Related U.S. Application Data

[62] Division of Ser. No. 557,329, Jul. 23, 1990, Pat. No. 5,179,015.

[51] Int. Cl.$^5$ .................... C12N 15/55; C12N 9/22
[52] U.S. Cl. ............................ 435/172.3; 435/193; 435/199; 435/252.33; 435/320.1; 536/23.2
[58] Field of Search ............ 435/172.3, 320.1, 252.33, 435/193, 199, 851; 536/23.2

[56] References Cited

PUBLICATIONS

Roberts, Nucleic Acids Res., 16:r271–313 (1988).
Wilson, Gene, 74:281–289 (1988).
Mann et al., Gene, 3:97–112 (1978).
Kosykh et al., Mol Gen. Genet., 178:717–718 (1980).
Walder et al., Proc. Natl. Acad. Sci. U.S.A., 78:1503–1507 (1981).
Bougueleret et al., Nucleic Acids Res., 12:3659–3676 (1974).
Kiss et al., Nucleic Acids Res., 13:6403–6421 (1985).
Slatko et al., Nucleic Acids Res., 15:9781–9786 (1987).
Karreman and DeWaard, J. Bacteriol., 170:2527–2532 (1988).
Szomolanyi et al., Gene, 10:219–225 (1980).
Janulaitis et al., Gene, 20:197–204 (1983).
Caserta et al., J. Biol. Chem., 262:4770–4777 (1987).
Chandrasegaran et al., Gene, 70:387–392 (1988).
Lunnen et al., Gene, 74:25–32 (1988).
McClelland and Nelson, Gene, 74:291–304 (1988).
Howard, et al., Nucleic Acids Res., 14:7939–7951 (1987).
Brooks, et al., Nucleic Acids Res., 17:979–997 (1989).
Slatko, et al., Gene, 74:45–50 (1988).

*Primary Examiner*—Charles L. Patterson, Jr.
*Attorney, Agent, or Firm*—David G. Conlin; David S. Resnick; Gregory D. Williams

[57] ABSTRACT

The present invention provides a novel approach to the production of restriction enzymes. More specifically, there is provided a novel method for cloning these enzymes, which comprises preparing DNA libraries from the DNA of an organism that synthesizes the restriction enzyme of interest, creating a suitable host containing a heterospecific methyltransferase gene able to protectively modify DNA from digestion by the restriction enzyme of interest, introducing the DNA libraries into the protectively modified host, and screening recombinant organisms to identify those carrying the desired restriction enzyme gene.

The application of this method to the FspI and HaeIII restriction genes of Fischerella species and *Haemophilus aegyptius*, respectively, is described in detail, together with the resulting clones that form the basis of a new and useful process for purifying the FspI and HaeIII restriction enzymes.

11 Claims, No Drawings

HETEROSPECIFIC MODIFICATION AS A MEANS TO CLONE RESTRICTION GENES

This is a division of copending application Ser. No. 07/557,329, filed on Jul. 23, 1990, now U.S. Pat. No. 5,179,015.

BACKGROUND OF THE INVENTION

The present invention relates to a procedure for cloning genes that encode restriction endonucleases, and to the gene products synthesized by such clones. The procedure makes use of the fact that certain modification genes, when cloned into a new host and adequately expressed, enable the host to tolerate the presence of a variety of different restriction genes. These artificial combinations of modification and restriction genes so created can be as stable, biologically, as the naturally-occurring combinations of restriction and modification genes. More specifically, the present invention relates to the use of the M.HhaI modification gene to facilitate the cloning of the R.FspI restriction gene, and to the use of the M.FnuDI modification gene to facilitate the cloning of the R.HaeIII restriction gene. The present invention also relates to the restriction enzymes synthesized from genes cloned by this procedure, and, more specifically, to the R.FspI and R.HaeIII restriction enzymes.

Restriction endonucleases ('ENases') are enzymes that occur mainly in bacteria; they function as simple immune systems that help cells to recover from infection by detrimental DNA molecules, such as viruses. Restriction endonucleases interact, with remarkable exactness, with particular sequences of nucleotides Within DNA molecules—'recognition sequences'—and break apart the molecules in the vicinity of these sequences. Breakage disrupts the genes and leads, eventually, to the disintegration of the entire DNA molecule. The process is termed 'restriction'.

Since bacteria contain DNA themselves, they have developed a way to protect their DNA from digestion by their own ENases. They do this by chemically altering the sequences in their DNA that would otherwise be recognized by the ENases. The ENases are unable to interact with, or cleave, the altered sequences. The process of alteration is termed 'modification'. Modification is carried out by enzymes—termed methyltransferases (MTases); it consists of the covalent attachment of a methyl group to one of the adenine or cytosine residues that occur in each strand of the recognition sequence. An ENase and a MTase, together, make up a restriction-modification ('R-M') system. Some bacterial species possess only one R-M system; others have several R-M systems, each acting independently at a different DNA sequence. The biological interdependence of ENases and MTases has become so intertwined over time that the genes encoding these enzymes ('R' and 'M' genes) have co-evolved, and occur together, for the most part, side-by-side, in bacterial chromosomes.

During the last fifteen years, restriction endonucleases, and to a lesser extent modification methyltransferases, have become useful laboratory reagents. The enzymes can be purified by conventional protein-purification techniques, and they can then be used to alter DNA molecules in the test tube. The altered DNA can be separated, analyzed, joined in new arrangements, and reintroduced into living cells. ENases, especially, provide the molecular biologist, the clinical researcher, and the forensic chemist, alike, with ways to dissect and to identify DNA molecules. Because of their usefulness, there is a strong incentive to develop strains of bacteria that yield high levels of restriction and modification enzymes. One way to achieve this is to transfer ('clone') the genes for an R-M system into a new host cell, under circumstances where the genes can then be over-expressed. The present invention concerns a new approach to cloning restriction genes; the approach is exemplified by the cloning of the genes for the FspI and HaeIII systems into *Escherichia coli*.

Many hundreds of restriction-modification systems have been discovered (Roberts, R., *Nucleic Acids Res.* 16: r271-313 (1988)), and a substantial number—approximately fifty—have now been cloned, in full or in part (Wilson, G., *Gene* 74: 281-289 (1989)). To clone an R gene, it is usually also necessary to clone the companion M gene, so that the recipient cell has the wherewithal to protect its DNA from digestion by the new ENase. Cloning an R gene thus becomes, in practice, a matter of cloning both R and M genes. Two general selection procedures have been used to isolate such clones. The first step in both procedures is the construction of a DNA library, consisting of fragments of bacterial DNA ligated into a plasmid vector, and introduced into a new host, usually *E. coli*. The first procedure selects, in vivo, for clones that express the restricting phenotype: the library of cells is incubated with bacterial viruses, and cells that survive are collected. The second procedure selects, in vitro, for clones that express the modifying phenotype: the library of recombinant plasmids is incubated with a restriction enzyme that cleaves unmodified DNA, and surviving molecules are collected following transformation into a host cell.

The first procedure yields clones that carry the complete R-M system (Mann et al., *Gene* 3: 97-112 (1978); Kosykh et al., *Mol. Gen. Genet.* 178: 717-718 (1980); Walder et al., *Proc. Natl. Acad. Sci.* USA 78: 1503-1507 (1981); Bougueleret et al., *Nucleic Acids Res.* 12: 3659-3676 (1984)). In practice, however, this method is fraught with difficulties, and it is often not successful. The second procedure yields both clones that carry the complete R-M system (Kiss et al., *Nucleic Acids Res.* 13: 6403-6421 (1985); Slatko et al., *Nucleic Acids Res.* 15: 9781-9786 (1987); Karreman and De Waard, *J. Bacteriol.* 170: 2527-2532 (1988)), and clones in which only the M gene is intact (Szomolanyi et al., *Gene* 10: 219-225 (1980); Janulaitis et al., *Gene* 20: 197-204 (1983); Caserta et al., *J. Biol. Chem.* 262: 4770-4777 (1987); Chandrasegaran et al, *Gene* 70: 387-392 (1988)). The second procedure is not altogether free of problems (Lunnen et al., *Gene* 74: 25-32 (1988)), but it is successful on most occasions, and so it has become the method of choice for scientists working in this area.

In some instances, methylation by a particular MTase protects the DNA from cleavage not only by the companion ENase, but by related ENases, too. This happens when the recognition sequences of the ENases are the same as, or are subsets of, the recognition sequence of the MTase. For example, methylation by the M.FnuDI MTase (recognition sequence, GGCC) blocks cleavage by not only the R.FnuDI ENase (GGCC), but also by the isoschizomers, R.HaeIII, R.BsuRI, and R.NgoPII (GGCC), and by R.AatI (AGGCCT), R.ApaI (GGGCCC), R.BalI (TGGCCA), R.EaeI (PyGGCCPu), R.EagI (CGGCCG), and R.NotI (GCGGCCGC) (see McClelland and Nelson, *Gene* 74: 291-304 (1988) for a compilation of protective modifications). In such instances, once an initial MTase gene has been cloned, in order to clone the related restriction genes, it ought not to be necessary to clone their companion MTase genes as well, since the initial MTase can substitute for all of them. Thus, if the gene for the M.FnuDI MTase were cloned, to continue the example, cells containing that gene could be used as recipients for the cloning of the R.HaeIII, R.BsuRI, R.NgoPII, R.AatI, R.ApaI, R.BalI, R.EaeI, R.EagI, and R.NotI ENase genes. The R genes could be cloned independently of their companion M genes; only the R genes would need to be cloned, and not the full R-M systems.

We refer to situations where one MTase can substitute for a number of other MTases as 'heterospecific modification'. There are several circumstances under which one might want to take advantage of the phenomenon of heterospecific modification. During manipulation of an R-M system, to overexpress the R gene for example, it could be beneficial to remove the companion M gene to increase the accessibility of the R gene. This could be accomplished rather easily if a heterospecific M gene were present to compensate for the loss of the normal MTase. Also, since it is usually more straightforward to clone a single gene, rather than two genes, it should be easier to clone an R gene on its own, than it would be to clone a complete R-M system. Thus, provided that ENase-containing clones could be reliably selected or identified, isolating a new R gene clone under conditions of preexisting, heterospecific modification should be more efficient than attempting to isolate it together with its companion M gene. Certain R-M systems cannot, in fact, be cloned directly in a single step, anyhow (Howard et al., *Nucleic Acids Res.* 14: 7939-7951 (1987); Brooks et al., *Nucleic Acids Res.* 17: 979-997 (1989)). In these instances, the protection afforded by the cloned companion M gene appears to be inadequate, and as a result, recipient cells succumb to digestion by the new ENase. It is only possible to clone these systems if the recipient cells are already modified prior to the arrival of the R gene. Premodification can, admittedly, be accomplished using a previously cloned companion MTase (Howard et al., 1987; Brooks, et al., 1989), but using a heterospecific MTase, instead, has several advantages, including broader applicability and the absence of DNA sequence homology. The absence of DNA sequence homology enables previously cloned parts of the R-M system to be used as probes to detect the presence of the R gene.

We describe here the application of heterospecific modification to the cloning into *E. coli* of two R-M systems: the FspI R-M system (TGCGCA) from Fischerella species, the cloning of which was facilitated by the the hhaIM MTase gene (GCGC); and the HaeIII R-M system (GGCC) from *Haemophilus aegyptius*, the cloning of which was facilitated by the fnuDIM gene (GGCC). The examples demonstrate the utility of heterospecific modification as a means for cloning ENase genes or complete R-M systems.

SUMMARY OF THE INVENTION

In accordance with the present invention, there is provided a novel approach to the production of restriction enzymes. More specifically, there is provided a novel method for cloning these enzymes, which comprises preparing DNA libraries from the DNA of an organism that synthesizes the restriction enzyme of interest, creating a suitable host containing a heterospecific methyltransferase gene able to protectively modify DNA from digestion by the restriction enzyme of interest, introducing the DNA libraries into the protectively modified host, and screening recombinant organisms to identify those carrying the desired restriction enzyme gene.

The application of this method to the FspI and haeIII restriction genes of Fishererlla species and *Haemophilus aegyptius*, respectively, is described in detail, together with the resulting clones that form the basis of a new and useful process for purifying the FspI and HaeIII restriction enzymes.

DETAILED DESCRIPTION OF THE INVENTION

The methods described herein by which restriction genes are preferably cloned and expressed include the following steps:

Step 1. A restriction enzyme, the gene (R) for which one wishes to clone, is identified. The DNA of the organism that synthesizes the restriction enzyme is purified.

Step 2. A methyltransferase from an R-M system other than the R-M system of Step 1, and able to protectively modify DNA from digestion by the restriction enzyme, is identified. The gene for the methyltransferase (M') is cloned, for example, using the procedure described by Lunnen, et al., *Gene* 74:25-32 (1988). The gene is transferred to a suitable host and its expression is adjusted, if necessary, to ensure that the host becomes fully modified.

Step 3. One or more libraries are prepared by recombining into a suitable cloning vector, such as pBR322, pBR328, pUC8, pUC9, pUC18 or pUC19, fragments of DNA from the organism that synthesizes the restriction enzyme. The libraries are introduced into the protectively modified host by for example, transformation or transduction, and recipient organisms carrying the recombinant molecules are selected.

Step 4. The recombinant organisms are screened to identify those among them that carry the desired R gene, using for example, the companion methylase gene as a probe, restriction of phages, hybridization to an oligonucleotide probe synthesized on the basis of the amino acid sequence of a section of the endonuclease, an antibody probe to the endonuclease, or an oligonucleotide recognition-sequence probe. Organisms found to carry the desired R gene are characterized. Depending on the original source for the R gene, and on the way in which the libraries were prepared, the desired recombinants may contain only the R gene, or they may contain the R gene together with its companion M gene. The cloned R gene is manipulated, if necessary, to achieve its overexpression.

For recovering the enzymes of the present invention, the clones obtained may be grown using any suitable technique, for example, the clones may be grown in Luria-broth, containing the appropriate antibiotics, and incubated at 37° C. with agitation and aeration. Cells in stationary phase are collected using centrifugation and stored frozen at −70° C.

After the cells are harvested and frozen, the enzyme can be isolated and purified from the frozen cell paste by using conventional enzyme purification methods. For example, the obtained cell paste is thawed and suspended in a buffer solution and subjected to treatment to allow extraction of the enzyme by the buffer solution, such treatment includes sonication, high pressure dispersion, or enzymatic digestion. The cell residue is then removed by centrifugation, and the supernatant containing the new enzyme can be purified by ion-exchange chromatography, using for example phosphocellulose or DEAE-cellulose, molecular sieve chromatography and affinity chromatography, using for example heparin agarose or DNA-cellulose, or a combination of these methods, to produce the enzyme of the present invention.

In applying the invention to our own needs, the four steps were performed in the following way:

Step 1. We sought to clone the genes for the R.FspI restriction enzyme (recognition sequence TGCGCA), from Fischerella species, and for the R.HaeIII restriction enzyme (recognition sequence GGCC), from *Haemophilus aegyptius*. Samples of these bacteria were obtained from the American Type culture collection (ATCC Nos. 29114 and 11116, respectively), the organisms were cultured, and their DNA was purified. Attempts were made to clone the FspI and HaeIII R-M systems into *E. coli*, by selection for the modification phenotype using the method described in Wilson, G., U.S. patent application Ser. No. 707,079, and as discussed in Lunnen et al., 1988. The attempts were not successful, although clones carrying the M gene from both of the R-M systems were recovered. From Fischerella, clones carrying the fspIM methylase gene were recovered (listed in Wilson, 1988), and from Haemophilus, clones carrying the haeIIIM methylase gene were recovered (reported in Slatko et al., *Gene.* 74: 45–50 (1988)). We assumed, correctly it turned out, that for both FspI and HaeIII, the R genes were adjacent to the M genes, but that they were not present in their entirety on the fragments that had been cloned.

Step 2. We had previously cloned into *E. coli* the genes for the M.HhaI methyltransferase (Caserta et al., 1987; Barsomian et al., *Gene* 74: 5–7 (1988)), and the gene for the M.FnuDI methyltransferase (Van Cott and Wilson, *Gene* 74: 55–59 (1988)). M.HhaI recognizes the sequence GCGC, and modification of FspI sites (TGCGCA) by M.HhaI was shown to protect them from cleavage by the R.FspI restriction enzyme. M.FnuDI recognizes GGCC, the same sequence as HaeIII, and modification of the sequence by M.FnuDI was also shown to protect the sequence from cleavage by the R.HaeIII restriction enzyme. The DNA fragments carrying the hhaIM and fnuDIM genes were transferred to the plasmid vector pACYC184, and the recombinant molecules were transformed into *E. coli* strains RR1 and ER1398, respectively. The DNAs of the transformants was shown to be resistant to digestion by R.RspI and R.HaeIII, respectively, and thus to be fully modified.

Step 3. The DNA fragment containing the cloned fspIM gene was gel-purified and nick-translated to prepare a radioactive hybridization probe specific for the FspI R-M genes. The fragment containing the cloned haeIIIM gene was treated similarly to prepare a probe specific for the HaeIII R-M genes. The probes were used initially in Southern blots of digested Fischerella and Haemophilus DNA to identify overlapping fragments that might include the respective R genes in their entirety. Genomic fragments thus identified were gel-purified, and then ligated into the compatible vector pUC19. The ligations were transformed into the appropriately modified *E. coli* host, the FspI ligations into cells carrying the hhaIM gene, and the HaeIII ligations into cells carrying the fnuDIM gene.

Step 4. Among the populations of transformants, individuals carrying DNA derived from the FspI and HaeIII R-M regions were identified by filter-hybridization to the gene-specific probes used earlier, in step 3. The clones were isolated and characterized with respect to the plasmids that they carried, and with respect to the enzymes that they synthesized. The clones that hybridized to the fspIM probe were found to carry both the fspIM and fspIR genes in their entirety, and to synthesize a high level of the R.FspI restriction enzyme. Likewise, the clones that hybridized to the haeIIIM probe were found to carry both the haeIIIM and haeIIIR genes in their entirety, and to synthesize a high level of the R.HaeIII restriction enzyme. Subsequent analysis of clones revealed why the our earlier attempts to clone the complete FspI and HaeIII R-M systems had been unsuccessful. On their own, the recombinant plasmids carrying the complete R-M systems were found to be extremely unstable in *E. coli*, presumably because the level of modification provided by their own M genes is insufficient to fully protect the hosts. Plasmids carrying the complete FspI R-M system were unable to transform *E. coli* unless the hhaIM gene was also present, either preexisting in the cells, or transformed simultaneously. Plasmids carrying the complete HaeIII R-M system were able to transform *E. coli* on their own, however, but the transformants were found to die within a few generations unless the fnuDIM gene was present.

In accordance with the present invention, there is provided a clone containing the fspIR and fspIM genes, coding for the R.FspI endonuclease and M.FspI methyltransferase, respectively, and a clone containing the haeIIIR and haeIIIM genes, coding for the R.HaeIII endonuclease and M.HaeIII methyltransferase, respectively. The fspIR and M genes derive from Fischerella species (ATCC No. 29114), and the haeIIIR and M genes derive from *Haemophilus aegyptius* (ATCC No. 11116). The endonucleases produced in accordance with the present invention are substantially pure and free of the contaminants normally found in R.FspI and R.HaeIII preparations purified from Fischerella sp. and *Haemophilus aegyptius*, respectively. The preferred method for cloning the genes for these endonucleases comprises forming libraries containing DNA from Fischerella sp. and *H. aegyptius*, transforming the libraries into a strain of *E. coli* protectively modified at FspI sites and at HaeIII sites, respectively, by the action of previously cloned, heterospecific methylase genes, such as hhaIM and fnuDIM, and isolating clones which contain DNA coding for the R.FspI and R.HaeIII endonucleases.

EXAMPLES

The following examples are given to illustrate embodiments of the present invention as it is currently preferred to practice it. It will be understood that the examples are illustrative, and that the invention is not to be considered as restricted thereto except as indicated in the appended claims.

EXAMPLE 1

Cloning of the FspI Restriction-Modification System

Step 1: Cloning of the fspIM Modification Gene

A 3.5-kb HindIII-fragment of Fischerella sp. DNA, containing the gene coding for the M.FspI modification methyltransferase, was cloned into *E. coli* strain K802. The procedure used was selective in nature, and of general applicability; its strengths and weaknesses are discussed at length in Lunnen et al., *Gene* 74: 25-32 (1988). The procedure is summarized in this section.

1.1 Purification of Fischerella sp. DNA: 3 g of Fischerella sp. (ATCC No. 29114) cell paste was ground in liquid nitrogen for approximately 10 min, to disrupt the cell walls. When the paste had been reduced to a powder, it was resuspended in 10 ml of 50 mM Tris pH 8.0, 0.1 M EDTA, 25% sucrose, 3 mg/ml lysozyme. The suspension was incubated at 37° C. for 1 h. 0.5 ml of 20% SDS, and 0.1 ml of 150 µg/ml of proteinase K were added and incubation was continued at 37° C. After 5 h, 5 ml of 0.1M Tris pH 8.0, 0.1M EDTA and 1.0 ml of 20% SDS were added, and incubation was continued at 45° C. to 50° C. overnight. The solution was extracted once with 17 ml of phenol, twice with 17 ml of chloroform, and once with 17 ml of ether. The DNA was precipitated at −20° C. by the addition of NaCl to 0.4 M, and 2 vol of ethyl alcohol. The precipitated DNA was resuspended in 10 mM Tris, pH 8.0, 1 mM EDTA, digested with RNase, and then stored at 4° C.

1.2 Partial digestion of Fischerella sD DNA: 10 ug of Fischerella sp. DNA was diluted into 200 µl of restriction endonuclease digestion buffer (10 mM Tris pH 7.5, 10 mM MgCl$_2$, 10 mM mercaptoethanol, 50 mM NaCl). The solution was dispensed into 5 tubes, 60 µl into the first tube and 30 µl into each of the remaining tubes. 20 u of HindIII (1 µl) was mixed into the first tube to achieve 7 u enzyme/µg of DNA; 30 µl was withdrawn and transferred to the second tube (3.5 u/µg). 30 µl was then withdrawn from the second tube and transferred to the third tube, and so on, each transfer effecting a 2-fold serial dilution of HindIII. The tubes were incubated for 1 h at 37° C., then heated for 15 min at 72° C. to stop the reactions. 5 µl from each tube was analyzed by agarose gel electrophoresis. Tubes in which moderate, but incomplete, digestion had occurred were combined. Two additional digestion series were performed in a similar manner using Sau3AI and MspI.

1.3 Ligation and transformation: 3 µg (60 µl) of HindIII-digested Fischerella sp. DNA was mixed with 1.5 µg (8 µl) of HindIII-cleaved and dephosphorylated pBR322 (ATCC No. 37017). 10 µl of 500 mM Tris pH 7.5, 100 mM MgCl$_2$, 1100 mM DTT, 5 mM ATP, and 17 µl of sterile distilled water were added to bring the volume to 95 µl. 5 µl of T4 DNA ligase was added and the solution was incubated at 16° C. for 4 h. The solution was sterilized by extraction with 10 µl of chloroform, then clarified by microcentifugation for 15 s. 85 µl of the ligation solution was mixed with 700 µl of 50 mM NaCl, 5 mM Na$_3$Citrate, 67 mM CaCl$_2$ and 1.4 ml of ice-cold, competent *E. coli* K802 (ATCC No. 33526) cells were added. The solution was incubated at 44° C. for 4 min, then 12.5 ml of Luria-broth (L-broth) was added and incubation was continued at 37° C. for 3 h. Similar ligations were also set up between the Sau3AI digest of Fischerella sp. DNA and BamHI digested pBR322, and between the MspI digest of Fischerella sp. DNA and ClaI-digested pBR322. The additional ligations were also transformed into *E. coli* K802.

1.4 Fischerella sp. cell libraries: The transformed cultures were gently centrifuged, the supernatants were discarded, and the cells from each culture were resuspended in 1.0 ml of Luria-broth. 200 µl portions of the resuspended cells were plated onto Luria-agar (L-agar) plates containing 100 µg/ml ampicillin. The plates were incubated overnight at 37° C. The colonies that grew up were collected into three pools, one for each ligation, by flooding each plate with 2.5 ml of 10 mM Tris pH 7.5, 10 mM MgCl$_2$, and scraping the colonies together.

1.5 Fischerella sp. plasmid libraries: 2.0 ml of each cell library was inoculated into 500 ml of L-broth containing 100 µg/ml ampicillin. The cultures were shaken overnight at 37° C. then centrifuged at 4 Krpm for 5 min. The supernatants were discarded and the cell pellets were resuspended in 10 ml of 25% sucrose, 50 mM Tris pH 8.0, at room temperature. 5 ml of 0.25M EDTA, pH 8.0, and 3 ml of 10 mg/ml lysozyme in 0.25M Tris pH 8.0 was added to each. The solutions were kept on ice for 1 h, then 12 ml of 1% Triton X-100, 50 mM Tris pH 8.0, 67 mM EDTA was added to each, and the suspensions were gently swirled to induce cell lysis. The lysed mixtures were transferred to a 50 ml tubes and centrifuged for 45 min. at 17 Krpm, 4° C. The supernatants were removed with a pipette. 20.0 gm of solid CsCl was weighed into three 50 ml plastic screw-cap tubes and 22.0 gm of each supernatant was pipetted into each tube and mixed. 1.0 ml of 5 mg/ml ethidium bromide in 10 mM Tris pH 8.0, 100 mM NaCl, 1 mM EDTA was added to each tube. Each of the solutions was transferred to two ⅝ in. ×3 in. centrifuge tubes and spun in a Beckman Ti70 rotor for 42 h at 44 Krpm, 17° C. To collect the plasmid DNA in each tube, they were illuminated with ultraviolet light and the lower of the two fluorescent bands was collected by syringe. The ethidium bromide was removed from each of the collected bands by extracting four times with an equal volume of CsCl-saturated, isopropanol. The extracted solutions were dialyzed against 4 changes of DNA buffer, then the nucleic acids were precipitated overnight at −20° C. by the addition of 2 vol of isopropanol and NaCl to a final concentration of 0.4M. The solutions were centrifuged for 15 min at 15 Krpm, 0° C., the supernatants were discarded, the pellets were air-dried for 15 min and then each was dissolved in 500 µl of 10 mM Tris pH 7.5, 1 mM EDTA and stored at −20° C. The plasmid DNA concentrations were approximately 100 µg/ml.

1.6 Selective R.FspI-digestion: 1 µg quantities of the plasmid libraries in 100 µl of 10 mM Tris pH 7.5, 10 mM MgCl2, 10 mM mercaptoethanol, 10 mM NaCl, were digested with 0, 20, and 40 u of R FspI restriction endonuclease at 37° C. for 2 h. The reactions were terminated by heating to 72° C. for 12 min, then 20 µl (0.2 ug) of each was transformed into *E. coli* K802. The mixtures were plated onto Luria-agar plates containing 100 µg/ml ampicillin, and incubated overnight at 37° C. R.FspI-digestion reduced the number of transformants approximately 10$^3$-fold.

1.7 Analysis of survivors: Twenty colonies were picked from among the survivors of each library. Each colony was inoculated into 10 ml of Luria-broth containing 100 µg/ml ampicillin, and grown overnight at 37° C. Each of the plasmids present in the sixty isolates was prepared by the following miniprep purification procedure, adapted from Birnboim and Doly, *Nucleic Acids Res.* 7:1513 (1979).

Each culture was centrifuged at 8 Krpm for 5 min; the supernatant was discarded and the cell pellet was resuspended in 1.0 ml of 25 mM Tris, 10 mM EDTA, 50 mM glucose, pH 8.0, containing 1 mg/ml lysozyme. After 10 min at room temperature, 2.0 ml of 0.2M NaOH, 1% SDS was added to each tube; the tubes were shaken to lyse the cells, then they were placed on ice. Once the solutions had cleared, 1.5 ml of 3M sodium acetate, pH 4.8, was added to each and shaken. The precipitates that formed were spun down at 15 Krpm, 4° C. for 10 min. Each supernatant was poured into a centrifuge tube containing 3 ml of isopropanol and mixed. After 10 min at room temperature, the tubes were spun at 15 Krpm for 10 min to pellet the precipitated nucleic acids. The supernatants were discarded and the pellets were air-dried at room temperature for 30 min. Once dry, the pellets were resuspended in 850 μl of 10 mM Tris, 1 mM EDTA, pH 8.0. 75 μl of 5M NaCl was added to each and the solutions were transferred to Eppendorf tubes containing 575 μl of isopropanol, and again precipitated for 10 min at room temperature. The tubes were then spun for 45 s in a microfuge, the supernatants were discarded and the pellets were air-dried. The pellets were then dissolved in 500 μl of 10 mM Tris, 1 mM EDTA, pH 8.0, containing 100 μg/ml RNase and incubated for 1 h at 37° C. to digest the RNA. The DNA was precipitated once more by the addition of 50 μl of 5M NaCl followed by 350 μl of isopropanol. After 10 min at room temperature, the DNA was spun down by centrifugation for 45 s, the supernatants were discarded and the pellets were redissolved in 150 μl of 10 mM Tris 1 mM EDTA, pH 8.0. The plasmid minipreps were subsequently analyzed by digestions with FspI, HindIII, Sau3AI and MspI.

1.8 Identification of fspIM clones: Forty-seven of the sixty plasmids that were analyzed were found to be sensitive to FspI-digestion and to carry diverse fragments of Fischerella sp. DNA. These plasmids were spurious and they were discarded. The remaining 13 plasmids were found to be resistant to FspI-digestion and to carry a segment in common that contained a HincII and EcoRV site. None of the clones synthesized the R.FspI endonuclease, leading us to believe that none of them carried the intact FspIR gene. One of the clones from the HindIII-library, containing a single 3.8-kb HindIII-fragment ligated into the HindIII site of pBR322, was retained. The plasmid was designated pMMfspIM 2-4.

Step 2: Cloning of the hhaIM Gene, and Modification of E. coli

A 1.5-kb HindIII-fragment of *Haemophilus haemolyticus* DNA, containing the gene coding for the M.HhaI modification methyltransferase, was cloned into *E. coli* strain RR1 as described in Caserta et al., *J. Biol. Chem.* 262: 4770–4777 (1987). The procedure used was similar to that described above for cloning the FspIM gene; the procedure is summarized in this section.

2.1 *H. haemolyticus* DNA purification: 10 g of frozen *Haemophilus haemolyticus* cells (ATCC No. 10014) were thawed on ice for 1 h, then resuspended in 20 ml of 25% sucrose, 50 mM Tris pH 8.0. 10 ml of 0.25M EDTA pH 8.0, and 6 ml of 10 mg/ml lysozyme in 0.25M Tris pH 8.0 were added. The suspension was kept on ice for 2 h, then lysed by the addition of 24 ml of 1% Triton X-100, 50 mM Tris pH 8.0, 67 mM EDTA and 5 ml of 10% SDS. The solution was extracted with 70 ml of phenol, (previously equilibrated with 0.5M Tris pH 8.0), and 70 ml of chloroform. The emulsion was centrifuged at 10 Krpm for 30 min and the viscous upper layer was withdrawn. The layer was reextracted with phenol:chloroform, and the emulsion was again centrifuged to separate the phases. The upper layer was withdrawn and dialyzed against four changes of 10 mM Tris pH 8.0, 1 mM EDTA. The dialyzed solution was then digested with RNase at a final concentration of 100 μg/ml for 1 h at 37° C. The DNA was then precipitated by adding NaCl to a final concentration of 0.4M, overlaying with 0.55 vol of isopropyl alcohol, and spooling the DNA onto a glass rod by mixing the phases together. The DNA was resuspended in DNA buffer (10 mM Tris pH 8.0, 1 mM EDTA) and stored at 4° C.

2.2 HindIII-digestion of *H. haemolyticus* DNA: The purified DNA was cleaved with HindIII as follows: 100 μg of *H. haemolyticus* DNA in 1 ml of 10 mM Tris pH 7.5, 10 mM MgCl$_2$, 50 mM NaCl, 10 mM mercaptoethanol, 0.005% Triton X-100, was prepared and dispensed into 9 tubes, 200 μl into the first tube and 100 μl into each of the remaining tubes. 40 u of HindIII (2 μl) was mixed into the first tube to achieve 2 u enzyme/μg of DNA; 100 μl was withdrawn and transferred to the second tube (1 u/μg). 100 μl was then transferred from the second to the third tube and so on, each step effecting a 2-fold serial dilution of HindIII. The tubes were incubated for 1 h at 37° C., heated for 15 min at 72° C. to stop the reactions, and 10 μl from each was analyzed by agarose gel electrophoresis. Tubes in which moderate, but incomplete, digestion had occurred were combined.

2.3 Ligation and transformation: 40 μl (4 μg DNA) of the combined solution was mixed with 10 μl of HindIII-cleaved and dephosphorylated pBR322 (2 μg; ATCC No. 3707). 10 μl of 500 mM Tris pH 7.5, 100 mM MgCl2, 100 mM DTT, 5 mM ATP was added, together with 40 μl of water and 250 u of T4 DNA ligase (2.5 μl). The mixture was incubated for 4 h at 16° C. The ligation was terminated by extraction with 20 μl of chloroform, and the mixture was transformed into 2 ml of competent *E. coli* RR1 (ATCC No. 31343).

2.4 *H. haemolyticus* cell library; The transformed cells were grown to saturation in 50 ml of Luria-broth, centrifuged, resuspended in 2.5 ml of Luria-broth, and 250 μl quantities were plated onto Luria-agar plates containing 50 μg/ml ampicillin. After overnight incubation at 37° C., the plates were each flooded with 3 ml 10 mM Tris pH 7.5, 10 mM MgCl$_2$ and the transformed colonies were scraped together and combined to form the cell library.

2.5 *H. haemolyticus* plasmid library: The cell library was inoculated into 500 ml of Luria-broth containing 50 μg/ml ampicillin and grown to saturation at 37° C. The cells were processed essentially as described in section 1.5, above, to purify the population of recombinant plasmids that they carried. The purified plasmid DNA was stored in 10 mM Tris pH 8.0, 1 mM EDTA.

2.6 Selective R.HhaI-digestion: 300 μl of plasmid DNA, at 50 μg/ml in 50 mM Tris pH 8.0, 5 mM MgCl2, 0.5 mM DTT, was prepared and dispensed into 5 tubes, 100 μl into the first tube and 50 μl into each of the remaining tubes. 100 u of HhaI restriction endonuclease (5 μl) was mixed into the first tube (20 u/μg); 50 μl was then withdrawn and mixed into the second tube (10 u/μg), and so on, each step achieving a 2-fold serial dilution of HhaI. The tubes were incubated for 1 h at 37° C., the reactions were terminated by extraction with 20 μl of chloroform, and the completeness of digestion checked by gel electrophoresis. 10 μl from each tube was transformed into competent *E. coli* RR1 and the transformed cells were plated onto Luria-agar plates containing 50 μg/ml ampicillin. After incubation the plates were examined; digestion of the library reduced the number of transformants from each tube by a factor of approximately $10^4$ compared to the undigested control.

2.7 Identification of hhaIM clones: The plasmids harbored by individual transformants were purified by the alkaline SDS miniprep procedure described in section 1.7, above, and analyzed by restriction endonuclease digestion and gel electrophoresis. Most of the plasmids were found to carry a single 1.5-kb fragment insert, and to display complete resistance to digestion by R.HhaI and R.HaeII. One such plasmid, designated pDNhhaIM 2-1, was retained. The nt sequence of the fragment present in pDNhhaIM 2-1 was determined. The fragment was found to include the 984-bp hhaIM gene in its entirety (Caserta et al., 1987); the gene for the HhaI restriction enzyme, hhaIR. was found not to be present on the fragment.

2.8 Transfer of the hhaIM gene to pACYC184: 2 µg of purified pDNhhaIM 2-1 DNA was mixed with 2 µg of pACYC184 DNA and digested, in 10 mM Tris pH 7.5, 10 mM MgCl$_2$, 50 mM NaCl, 10 mM mercaptoethanol, with 20 u of HindIII for 2 h at 37° C. The mixture was extracted with phenol:chloroform, and the DNA was precipitated with isopropanol. The digested DNA was resuspended in 90 µl of distilled water and 10 µl of 500 mM Tris pH 7.5, 100 mM MgCl$_2$, 100 mM DTT, 5 mM ATP was added. 250 u (2.5 µl) of T4 DNA ligase was mixed in, the DNA was ligated overnight at 16° C., and then it was transformed into *E. coli* RR1. The transformation mixture was plated onto Luria-agar plates containing 200 µg/ml chloramphenicol to select for transformants that had acquired the pACYC184 plasmid. 200 Cm$^R$ transformants were picked and patched onto plates containing 100 µg/ml ampicillin and 35 µg/ml tetracycline. Five transformants were found to be sensitive to ampicillin and tetracycline. The plasmids carried by these transformants were prepared and analyzed. All five plasmids were found to consist of pACYC184 with the 1.5-kb fragment inserted at the HindIII site. One clone, designated pJBhhaIM 302-1, was retained. A culture of *E. coli* RR1 harboring this plasmid was grown, and was processed to make the cells competent for DNA uptake. Both the plasmid DNA, and the chromosomal DNA, of this strain were completely resistant to digestion by R.HhaI. The strain was designated RR1 [pJBhhaIM 302-1].

Step 3: Creation of New FspI Libraries in M.HhaI-Modified *E. coli*

We assumed that the fspIR gene was located next to the fspIM gene in the chromosome of Fischerella sp. We further assumed that our failure to isolate clones that carried both genes was due to a fundamental biological barrier, namely that the fspIR gene was detrimental to unmodified *E. coli* cells. In order to clone the R gene, therefore, we needed to do two things: to identify larger fragments that spanned more of the chromosome of Fischerella sp. than did the fragments already isolated, and to move these fragments into *E. coli* cells that were already fully protected against digestion by the R.FspI endonuclease. We chose to use the hhaIM gene to achieve protection, rather than the fspIM gene, a strategy that enabled us subsequently to use the latter gene as a hybridization probe for the purpose of recognizing the new clones.

3.1 Preparation of radioactively labeled pMMfspIM 2-4: pMMfspIM 2-4 plasmid DNA was purified and nick-translated to prepare a hybridization probe for Southern blots. 1 µg (9 µl) of plasmid DNA was mixed with 2 µl of 10 X nick-translation buffer (0.5M Tris.HCl, pH 7.2, 0.1M MgSO$_4$, 1 mM DTT, 500 µg/ml bovine serum albumin); 2 µl of 0.1M MgCl$_2$; 2 µl of 10 nM each dATP, dCTP, dGTP, dTTP; 5 µl of [$^{32}$P]-dATP (Amersham; 800 Ci/mMol, 20 mCi/ml); 3 µl (30 u) of *E. coli* DNA polymerase I (New England Biolabs); and 2 µl of DNase I (0.1 µg/ml). The mixture was incubated at 15° C. for 20 min, then the reaction was stopped by the addition of 100 µl of 10 mM EDTA, pH 8.0. Unincorporated counts were removed by minicolumn chromatography through an 'Elutip' (Schleicher and Schuell).

3.2 Identification of overlapping fspIM gene fragments: Fischerella sp. DNA was digested separately with the restriction endonuclease AatII, SmaI, AvaI, BanII, HincII, XbaI, SspI, AccI, KpnI, SacI and SalI. The digests were electrophoresed on a 1.0% agarose gel. The gel was soaked in 0.25M HCl for 15 min; 0.5M NaOH, 1M NaCl for 30 min; and then in 1M Tris.HCl pH 7.5, 3M NaCl for 30 min. A nitrocellulose sheet was soaked in water for 1 h, then briefly immersed in 5 X SSC (0.75M NaCl, 75 mM Na$_3$Citrate). The sheet was applied to the surface of the gel and backed with chromatography paper (Whatman) to act as a wick. The sandwich was weighted down and transfer of the gel contents to the nitrocellulose sheet was allowed to proceed overnight at room temperature. The sheet was then baked in a vacuum oven at 8° C. for 1 h. to fix the transferred DNA fragments to the nitrocellulose support. The sheet was transferred to a plastic bag containing 15 ml of a solution composed of 3 ml of 10 gm/L Ficoll, 10 gm/L polyvinylpyrrolidone, 10 gm/L bovine serum albumin; 4.5 ml of 3M NaCl, 0.3M Na$_3$Citrate; 1.5 ml 10% SDS; 3 ml 10 % dextran sulfate; 3 ml water, and prehybridized by incubating at 63° C. for 1 h. The entire radioactive probe was added to the bag, and incubation was continued overnight. The nitrocellulose sheet was then washed at 60° C. three times with 20 mM Tris.HCl. pH 7.8, 1 mM EDTA, 0.15M NaCl, air-dried, then autoradiographed overnight. The probe hybridized to a single, 8-kb, band in both the XbaI-digest and the AccI-digest, and to 14-kb, band in the ClaI-digest. These bands were judged to be of suitable size for cloning, and to be likely to contain the fscIR gene as well as the fspIM gene.

3.3 Preparation of Fischerella sp. libraries: In separate reactions, Fischerella sp. DNA was digested to completion with XbaI, ClaI, and AccI. The reactions were stopped by heating to 72° C. for 15 min. 1 µg of each of the digested DNAs was combined with 1 µg of XbaI-cleaved and dephosphorylated pUC19 DNA, or AccI-cleaved and dephosphorylated pUC19 DNA (ATCC No. 37017), as appropriate. 5 µl of 500 mM Tris pH 7.5, 100 mM MgCl2, 100 mM DTT, 5 mM ATP was added, and the vol of each reaction was brought to 50 µl with water. 2.5 µl of T4 DNA ligase was added to each mixture, and ligation was carried out at 16° C. overnight. The ligations were terminated by extraction with 10 µl of chloroform, and then the mixtures were transformed separately into competent *E. coli* RR1 [pJBhhaIM 302-1]. The transformation mixtures were diluted into Luria-broth and incubated at 37° C. for 1 h to allow expression of the plasmid-borne antibiotic-resistance genes to occur, then the cultures were plated onto Luria-agar plates containing 200 µg/ml chloramphenicol and 100 µg/ml ampicillin. The plates were incubated overnight at 37° C.

3.4 Preparation of fspIM gene probe: A 2.3-kb BamHI to EcoRI subfragment of the 3.8-kb HindIII insert carried in pMMfspIM 2-4 was gel-purified and nick-translated. 30 μg of the plasmid DNA was incubated at 37° C. for 1 h in 10 mM Tris pH 7.5, 10 mM MgCl$_2$, 100 mM NaCl, 10 mM mercaptoethanol with 120 u each of R.BamHI and R.EcoRI. The digest was fractionated by gel electrophoresis on a 1.0% tris-acetate agarose gel. The gel was run for 2.5 h, at 100 mA, then illuminated with long-wave UV light and the 2.3-kb band was cut out of the gel and transferred to a syringe. The gel slice was extruded through an 18 gauge needle into a 5 ml centrifuge tube. The tube was centrifuged at 43 Krpm for 45 min at 25° C. in a Beckman SW 50.1 rotor. The supernatant was collected and the DNA was precipitated at −70° C. for 1 h by the addition of NaCl to 0.5M, and 2 vol of isopropanol. The precipitated DNA was resuspended in 500 μl of 10 mM Tris.HCl pH 8.0, 1 mM EDTA. The DNA was nicked translated using the procedure outlined in section 3.1, above.

STEP 4: Isolation and Characterization of fspIR Gene Clones

New libraries, consisting of Fischerella sp. DNA inserted into the plasmid pUC19, were prepared in *E. coli* RR1 [pJBhhaIM 302-1]. Colonies Were screened for hybridization to the 3.5-kb HindIII fragment containing the fspIM gene. Several new clones were identified that proved to carry the complete fspIR gene as well as the fspIM gene.

4.1 Isolation of overlapping fspIM gene fragments: The colonies representing the new libraries prepared as described in section 3.3, above, were transferred to nitrocellulose filters by contact-lifts. The filters were immersed in 0.5M NaOH, 2M NaCl for 30 s; 0.5M Tris.HCl, pH 7.5, 3M NaCl for 1 min; 0.3M NaCl, 0.03M Na$_3$Citrate, 0.1% SDS for 5 s; 0.3M NaCl, 0.03M Na$_3$Citrate for 10 s. The filters were air-dried, and then they were baked in a vacuum-oven at 80° C. for 30 min. The filters were prehybridized, and then hybridized with the 2.3-kb fspIM gene probe, using the procedure described in section 3.2, above. The filters were air-dried, and then they were autoradiographed overnight.

4.2 Identification of fspIR gene clones: approximately 10,000 colonies were screened from the XbaI-library; of these, five colonies hybridized strongly to the probe. The five clones were analyzed; four were found to carry the sought-after, 7.8-kb XbaI-fragment, and the fifth was found to be spurious. Similar numbers of colonies were also screened from the AccI-library and the ClaI-library, but no strongly-hybridizing colonies were found. One of the positive XbaI clones was retained and analyzed. The new plasmid carried by the clone contained all of the Fischerella sp. DNA present in pMMfspIM 2-4, and thus contained the complete fspIM gene. An extract of the clone was assayed for restriction endonuclease activity (section 4.3, below), and R.FspI activity was detected, confirming that the new plasmid also carried the complete fspIR gene. The new plasmid was designated pMMfspIRM 119-1, and the new bacterial strain was designated *E. coli* RR1 [pJBhhaIM 302-1, pMMfspIRM 119-1]

4.3 R.FspI restriction enzyme assay: Extracts of *E. coli* RR1 [pJBhhaIM 302-1, pMMfspIRM 119-1]were prepared and assay for restriction endonuclease activity. A 100 ml culture was grown overnight at 37° C. in Luria-broth containing 100 μg/ml ampicillin and 200 μg/ml chloramphenicol. The cells were pelleted by centrifugation at 4 Krpm for 5 minutes then resuspended in 3.0 ml of 10 mM KPO$_4$ buffer pH 7.5, 10 mM mercaptoethanol, 0.1 mM EDTA. 1 ml of the suspension was sonicated gently for three 10-s bursts to disrupt the cell walls, then it was centrifuged for 10 min in an Eppendorf centrifuge at 4° C. The supernatant was collected, and serially diluted in three-fold steps. An assay solution containing 33 μg/ml phage μ DNA in 10 mM Tris.HCl, pH 7.5, 10 mM MgCl$_2$, 50 mM NaCl was prepared, and 30 μl of the solution was dispensed into each of 5 tubes. 2 μl of the extract was added to the first tube; 2 μl of the first dilution of the extract was added to the second tube; 2 μl of the next dilution of the extract was added to the third tube, and so on. The first tube thus received 2 μl of extract/λg of μ DMA; the second tube, 0.67 μl/μg, the third tube 0.2 μl/μg and so on. The tubes were incubated at 37° C. for 1 h, then 2 μl of each was analyzed by gel electrophoresis. The titer of the cell extract was found to be approximately $7.5 \times 10^3$ u of R FspI restriction enzyme per ml, which corresponds to about $5 \times 10^4$ u per gram of wet cell paste. Fischerella sp. synthesizes approximately 500 u of R.FspI per gram, so the new clone represents a one hundred-fold improvement in yield. *E. coli* ER1398 [pJBhhaIM 302-1, pMMfspIRM 119-1]is the preferred host from which the FspI restriction endonuclease can be purified. The strain should be grown to stationary phase at 37° C. in a fermenter, in Luria-broth containing ampicillin and chloramphenicol. The cells should then be collected by centrifugation and either broken immediately for extract preparation, or stored frozen at −70° C. until it is convenient to do so.

4.4 Properties of pMMfspIRM 119-1: pMMfspIRM 119-1 was isolated in *E. coli* RR1 cells, all the FspI sites of which had been modified beforehand by the M.HhaI MTase. The MTase was furnished by another plasmid present in the cells, pJBhhaIM 302-1. We consider that the presence of pJBhhaIM 302-1 in the cells was a crucial factor that enabled pMMfspIRM 119-1 to be isolated. Two lines of evidence support this point of view:

4.4a Attempts to clone the fspIM gene from a library of XbaI-fragments of Fischerella sp. DNA in pUC19, using unmodified *E. coli* RR1 as the cloning host, and selecting for R.FspI-resistant molecules, were unsuccessful. A similar set of experiments, using Sau3AI, MspI, and HindIII-fragments, were successful, as documented in sections 1.6 to 1.8, above. We believe that the significant difference between these experiments is that the XbaI-fragment that carries the fspIM gene also carries the fspIR gene, whereas the HindIII, MspI and Sau3AI fragments that carry the FspIM gene, do not. We presume that the fspIM gene cannot protect the host well enough from restriction by the R.FspI ENase. Thus, while fragments that encode just the MTase are innocuous, those that encode the ENase also, are detrimental. In order to isolate fragments of the latter type, supplementary modification must be provided; we chose to use the M.HhaI MTase to provide supplementary modification, a strategy that proved to be effective.

4.4b When the plasmid DNA present in *E. coli* RR1 [pJBhhaIM 302-1, pMMfspIRM 119-1]was purified, a mixture of both plasmids was obtained. The plasmid pMMfspIRM 119-1 was the predominant plasmid in the mixture since its copy number in the host far exceeded that of pJBhhaIM 302-1. The mixture of plasmids was transformed, at a low multiplicity of transformation, into competent, unmodified, *E. coli* RR1 cells and transformants that had acquired the fspIRM plasmid were specifically selected-for by plating onto Luria-agar plates that contained 100 μg/ml ampicillin. 200 Ap® transformants were patched onto plates containing chloramphenicol to determine how many had simultaneously acquired the hhaIM plasmid. All of them appeared to have done so, a conclusion that was confirmed by direct examination of the plasmids present in a small number of randomly-chosen transformants. This suggests that, among the population of cells that received the fspIRM plasmid, only the subpopulation that had also received the second plasmid were able to survive and grow into colonies. Evidently, the presence of the second plasmid, which furnishes supplementary MTase, is essential for the survival of cells carrying the cloned FspI R-M system.

Although the above-outlined steps represent the preferred mode for practicing the present invention, it will be apparent to those skilled in the art that the above described approach can vary in accordance with techniques known in the art. Thus, although we used the M.HhaI MTase to clone the R.FspI ENase, this example represents only one of a large number of possible MTase-ENase substitution-type experiments. Although in this example we chose to clone the fspIM gene initially, and then to use it as a probe to identify subsequent clones that contained the adjacent fspIR gene, it is to be understood it will not always be necessary to perform this step. If we had had another way to identify clones carrying the R gene, by restriction of phages, for example, or by hybridization to an oligonucleotide probe synthesized on the basis of the amino acid sequence of a section of the endonuclease, or an antibody to the bind to the endonuclease, or an oligonucleotide recognition-sequence probe, then the initial cloning of the companion M gene could have been omitted altogether. Further, although we ended up, in fact, by cloning the FspI R and M genes, together, into cells containing the M.HhaI gene, it should be understood that the M.FspI gene was actually superfluous, and that its presence was in no way necessary to ensure the cloning of the R.FspI gene. Had it been more convenient to do so, we could have cloned just the R gene on its own into the M.HhaI-containing cells. Since the heterospecific methyltransferase modifies all of the sequences modified by the companion methyltransferase, and more besides, it substitutes completely for the latter. Advance modification by a heterospecific methyltransferase thus renders redundant the companion methyltransferase, and the presence, or otherwise, of the companion M gene on the fragment containing the R gene becomes functionally irrelevant.

EXAMPLE 2

Cloning of the HaeIII Restriction-modification System.

A 1.4-kb EcoRI-fragment of *Haemophilus aegyptius* DNA containing the haeIIIM gene, coding for the M.HaeIII methyltransferase, was cloned into *E. coli* strain RR1. The method used to isolate the clone was similar to that used for the fspIM and hhaIM genes, described in steps 1 and 2 of EXAMPLE 1, above. The procedure has been published, along with the entire nucleotide sequence of the fragment (Slatko et al., *Gene* 74: 45-50 (1988)), and so it will not be repeated here.

STEP 2: Cloning of the fnuDIM Gene and Modification of *E. coli*

5.5-kb HindIII-fragment of *Fusobacterium nucleatum* D DNA, containing the fnuDIM gene, coding for the M.FnuDI methyltransferase, was cloned into *E. coli* RR1. The procedure used was also similar to that described for the fspIM and hhaIM genes in steps 1 and 2 of EXAMPLE 1, above, and it has also been published (Van Cott, E. and Wilson, G., *Gene* 74: 55-59 (1988)). Only the subsequent steps, involving the construction of the M.FnuDI-modified *E. coli* host strain, will be described here.

2.1 The original fnuDIM gene clones: Several plasmid clones consisting of a 5.5-kb HindIII fragment of *F. nucleatum* DNA inserted into pBR322, and encoding the entire fnuDIM gene, were isolated (Van Cott, E. and Wilson, G., *Gene* 74: 55-59 (1988)). The plasmids were resistant to digestion by R.HaeIII, indicating that M.FnuDI-modification protects against cleavage by R.HaeIII, and that the plasmid DNA was fully modified. The fragment from one such plasmid, pEVCfnuDIRM 2-33, was transferred to the HindIII site . of pUC19 to make the plasmid pEVCfnuDIRM 102-1, which was deposited with the ATCC, No. 40521. Subsequently, most of the fragment in pEVCfnuDIRM 102-1—the DNA between the three HincII sites—was deleted, to make pEVCfnuDIM 102(26 delta)-1. This latter plasmid was used as the source from which the fnuDIM gene was transferred into pACYC184.

2.2 Transfer of the fnudIM gene into pACYC184: 0.1 $\mu$g of purified pEVCfnuDIM 102(26 delta)-1 DNA was digested with 8 u of HincII and 20 u of HindIII in a 30 $\mu$l volume of digestion buffer containing 10 mM Tris pH 7.5, 100 mM NaCl, 10 mM mercaptoethanol. Following a 1 h incubation at 37° C., the reaction was inactivated by a 10 min incubation at 70° C.. A 37° C. digestion of 0.1 $\mu$g purified pACYC184 DNA was carried out in a reaction containing 20 u EcoRV and 20 u HindIII in 10 mM Tris pH 7.5, 150 mM NaCl, 10 mM mercaptoethanol. This reaction was terminated after 1 h by a 70° C. incubation for 10 min. The digested DNAs were ligated together in a 10 $\mu$l reaction containing 0.03 $\mu$g pEVCfnuDIM 102(26 delta)-1, 0.03 $\mu$g pACYC184, and 1 $\mu$l ligation buffer (500 mM Tris, 100 mM MgCl$_2$, 100 mM DTT, 5 mM ATP, 100 u T4 DNA ligase). The ligation was incubated overnight at 16° C., and then transformed into *E. coli* ER1398. The transformants were plated onto Luria-agar plates containing 200 $\mu$g chloramphenicol, to select for transformants that had acquired the pACYC184 plasmid. Fourteen transformants were isolated and their plasmid DNAs were purified and analyzed. Two of the fourteen transformants contained the correct 1.4-kb fragment HincII to HindIII fragment coding for the fnuDIM gene; however, neither of these transformants displayed resistance to digestion by HaeIII, suggesting that they failed to synthesize the M.FnuDI methylase. This result was unexpected because the fnuDIM gene expresses well in both orientations in the original 5.5-kb HindIII fragment, in both pBR322 and pUC19.

A second experiment was therefore carried out to transfer the fnuDIM gene to pACYC184 in the reverse orientation. A 1 h, 37° C. digestion of 0.1 ug of purified pEVCfnuDIM 102(26D)-1 was made in a 30 ul volume of 10 mM Tris pH 7.5, 50 mM NaCl, 10 mM mercaptoethanol, 20 u of XbaI and 20 u of HindIII. The reaction was followed by a 10 min, 70° C. heat inactivation. A similar digestion and inactivation was performed with 0.1 $\mu$g of purified pACYC184 DNA. 0.03 $\mu$g of digested pEVCfnuDIM 102(26 delta)-1 was mixed with 0.01 $\mu$g of digested pACYC184 in 10 $\mu$l of 100 mM MgCl$_2$, 100 mM DTT, 5 mM ATP and 100 u T4 DNA ligase. Following an overnight incubation at 16° C., the ligation was transformed with *E. coli* ER1398, and plated onto Luria-agar plates containing 200 μg/ml chloramphenicol. The plasmids from eight transformants were prepared and analyzed. Two of the eight plasmids were found to be pACYC184 which contained the 1.4-kb fnuDIM fragment in the required orientation. The plasmids were completely resistant to digestion by R HaeIII. One of the plasmids, pMMfnuDIM 302:20-6 was retained. A culture of *E. coli* ER1398 harboring this plasmid, and designated ER1398 [pMMfnuDIM 302:20-6], was grown and was processed to make cells competent for DNA uptake.

STEP 3: Creation of haeIII Libraries in M.fnuDI-Modified *E. coli*

We assumed, correctly, that like the FspI R-M system, the genes of the HaeIII R-M system would lie together in the chromosome of *Haemophilus aegyptius*, and that the haeIIIM gene would not adequately protect *E. coli* from the activity of the haeIIIR gene. In order to clone the haeIIIR gene, then, we identified DNA fragments that spanned more of the chromosome of *H. aegyptius* than had already isolated, and we cloned these fragments into *E. coli* cells that were protected against R.HaeIII-digestion by the presence of the fnuDIM gene. Using the fnuDIM gene for protective modification, instead of the haeIIIM gene, allowed us to use the latter as a hybridization probe to identify the new, more extensive, HaeIII R-M system clones.

3.1 Preparation of radioactively labeled haeIIIM gene probe: The 1.4-kb EcoRI fragment containing the haeIIIM gene was excised from the plasmid pRChaeIIIM 1-2 by digestion with EcoRI. The digest was electrophoresed, and the 1.4-kb fragment was sliced from the gel with a razor blade, minced and then squeezed through an 18-gauge needle into a 50 ml tube containing 1 ml of 1X DNA buffer, 0.01% SDS. The solution was mixed, and then centrifuged at 15 Krpm for 30 min. The supernatent was retained and the DNA that it contained was precipitated with isopropanol. The precipitate was centrifuged at 15 Krpm for 10 min, and the pellet was dried, and then dissolved in 100 μl of 1 X DNA buffer. The solution was phenol/chloroform extracted, reprecipitated and then resuspended in 50 μl of 1 X DNA buffer to a final concentration of approximately 100 μg/ml. 0.5 μg (5 μl ) of the fragment was mixed with 1.5 μl of 10 X nick-translation buffer (50 mM Tris.HCl, pH 7.5, 5 mM MgCl₂, 1 mM mercaptoethanol); 1 μl of G,T,C mix (500 pMol of each nucleotide in dH₂O); 5 μl of [$^{32}$P]-dATP (Amersham; 800 Ci/mMol, 20 mCi/ml); 2 μl (20 u) of *E. coli* DNA polymerase I (New England Biolabs); and 1 μl of DNase I (1 μg/ml). The mixture was incubated at room temperature for 2 min, then placed at 16° C. for 2 h. The reaction was then heated to 100° C. for 10 min, and then placed on ice.

3.2 Identification of overlapping haeIIIM gene fragments: *Haemophilus aegyptius* DNA was digested separately with the following restriction endonucleases: EcoRI, HindIII, AvrII, ClaI, KpnI, BglII, BamHI, BclI, NheI, SphI, EcoRV, ScaI, SpeI, NsiI, PstI, AatII, XbaI, AccI, KpnI and SacI. The digestions were electrophoresed on a 1.0% agarose gel. The gel was denatured in 0.5M NaOH, 0.6M NaCl for 1 h, and then neutralized in 1M Tris.HCl pH 7.4, 0.6M NaCl for 2×30 min. A nitrocellulose sheet was immersed in the neutralizing buffer, then applied to the surface of the gel and backed with chromatography paper (Whatman) to act as a wick. The sandwich was weighted down and transfer of the gel fragments to the nitrocellulose sheet was allowed to proceed at room temperature overnight. The sheet was then baked in a vacuum oven at 80° C. for 2 h to fix the transferred DNA fragments to the nitrocellulose support. The sheet was transferred to a plastic bag containing 15 ml of a solution composed of 3 ml of 10 gm/L Ficoll, 10 gm/L polyvinylpyrrolidone, 10 gm/L bovine serum albumin; 4.5 ml of 3M NaCl, 0.3M Na3Citrate; 1.5 ml of 10% SDS; 3 ml of 10 % dextran sulfate; 3 ml of water, and prehybridized by incubating at 65° C. for 2 h. 10 ul of the radioactive 1.4-kb probe was added to the bag, and incubation proceeded at 65° C. overnight. The radioactive hybridization buffer was removed and the nitrocellulose sheet was then washed 4×5 min at room temperature with 2×SSC. The temperature was raised to 65° C., and the filter was washed 2×30 min with 2×SSC, 0.5% SDS. The filter was dried, and then autoradiographed overnight. The probe was found to hybridize to a single 8.5-kb SacI fragment, a single 5.5-kb PstI fragment, a single 11-kb ScaI fragment, and to two BplII fragments of 5.4 kb and approximately 14 kb. Analysis of the BglII fragments showed that the 5.4-kb fragment contained part of the haeIIIM gene and that it overlapped completely with previously cloned DNA; and that the 14-kb fragment contained the rest of the haeIIIM gene plus the DNA that ought to encode the entire haeIIIR gene. The fragments from the other digests were judged to be of suitable size for cloning, and to be likely to contain all of the haeIIIR gene as well as the haeIIIM gene.

3.3 Preparation of *Haemophilus aegyptius* libraries: In separate reactions, *H. aegyptius* DNA was digested to completion with BglII, PstI, SacI, ScaI. The reactions were stopped by heating to 70° C. for 10 min. 10 μg of each digest was electrophoresed, and fragments in the size-ranges of those identified by Southern blotting were gel-purified using the method described in section 3.1 of EXAMPLE 2. Approximately 1 μg of the gel-purified fragments were each combined with 1 μg of appropriately cleaved (BamHI, SacI, HincII, or. PstI-cleaved) and dephosphorylated pUC19 DNA. 6 μl of 500 mM Tris pH 7.5, 100 mM MgCl₂, 100 mM DTT, 5 mM ATP was added, and the vol of each reaction was brought to 60 μl with water. 1600 u of T4 DNA ligase was added to each mixture, and ligation was carried out at 16° C. overnight. The ligations were transformed separately into competent *E. coli* ER1398 [pMMfnuDIM 302:20-6]. The transformation mixtures were diluted into Luria-broth and incubated at 37° C. for 1 h to allow expression of the plasmid-borne antibiotic-resistance genes to occur, then the cultures were plated onto Luria-agar plates containing 200 μg/ml chloramphenicol and 100 μg/ml ampicillin. The plates were incubated overnight at 37° C..

STEP 4: Isolation and Characterization of haeIIIR Gene Clones

Libraries of *H. aegyptius* DNA, inserted into pUC19, were prepared in *E. coli* ER1398 [pMMfnuDIM 302:20-6]. The colonies were screened to identify those that carried an 8.5-kb SacI fragment expected to contain the entire HaeIII R-M system. Several such clones were isolated, and they were indeed found to carry the haeIIIR and M genes in their entirety.

4.1 Isolation of haeIIIR gene clones: The transformed populations were transferred to nitrocellulose filters by contact-lifts. The filters were immersed in 0.5M NaOH, 2M NaCl for 30 s; 0.5M Tris.HCl, pH 7.5, 3M NaCl for 1 min; 0.3M NaCl, 0.03M Na₃Citrate, 0.1% SDS for 5 s; and then 0.3M NaCl, 0.03M Na₃Citrate for 10 s. The filters were air-dried, and then baked in a vacuum-oven at 80° C. for 30 min. Following prehybridization, the filters were hybridized with the radioactively labeled 1.4-kb haeIIIM gene probe, as described in section 3.1 of EXAMPLE 2, above. The filters were air-dried, and then autoradiographed overnight.

4.2 Identification of the haeIIIR gene clones: Approximately 5000 colonies were screened from each of the four libraries, BglII, PstI, SacI, and ScaI. No strongly hybridizing colonies were found on the filters screened from the BglII, PstI, and ScaI libraries, but twenty-eight strongly hybridizing colonies from the SacI library were found. They were picked and assayed for HaeIII endonuclease activity. Eleven of the twenty-eight were found to synthesize R.HaeIII. One of the eleven positive SacI clones, designated pMMhaeIIIRM 127-1, was retained and analyzed. The plasmid was found to carry a single SacI fragment of the expected size, approximately 8.5 kb.

4.3 R.HaeIII restriction enzyme assay: Extracts of *E. coli* ER1398, carrying the plasmids pMMhaeIIIRM 127-1 and pMMfnuDIM 302:20-6, were prepared and assayed for restriction endonuclease activity. A 10 ml culture was grown overnight at 37° C. in Luria-broth containing 100 μg/ml ampicillin and 200 μg/ml chloramphenicol. The cells were pelleted by centrifugation at 7 Krpm for 5 min then resuspended in 1.0 ml of 10 mM KPO₄ buffer pH 7.5, 10 mM mercaptoethanol, 0.1 mM EDTA. The suspension was sonicated gently for 10 s to disrupt the cell walls, then it was centrifuged for 10 min in an Eppendorf centrifuge at 4° C. The supernatant was collected, and serially diluted in three-fold steps. An assay solution containing 33 μg/ml phage lambda DNA in 10 mM Tris.HCl, pH 7.5, 10 mM MgCl₂, 50 mM NaCl was prepared, and 30 μl of the solution was dispensed into each of 5 tubes. 2 μl of the extract was added to the first tube; 2 μl of the first dilution of the extract was added to the second tube; 2 μl of the next dilution of the extract was added to the third tube, and so on. The first tube thus received 2 μl of extract/μg of lambda DNA; the second tube, 0.67 μl/ μg, the third tube 0.2 μl/ μg and so on. The tubes were incubated at 37° C. for 1 h, then 20 μl of each was analyzed by gel electrophoresis. The titer of the cell extract was found to be approximately 5×10⁴ u of R.HaeIII restriction enzyme per ml, which corresponds to about 1×10⁶ u per gram of cell paste. *H. aegyptius* synthesizes approximately 2.5×10⁴ u of R.HaeIII per gram, so the new clone represents a forty-fold improvement in yield. *E. coli* ER1398 [pMMhaeIIIRM 127-1, pMMfnuDIM 302:20-6], NEB 603, is the preferred host from which the HaeIII restriction endonuclease can be purified. The strain should be grown to stationary phase at 37° C. in a fermenter, in Luria-broth containing ampicillin and chloramphenicol. The cells should then be collected by centrifugation and either broken immediately for extract preparation, or stored frozen at −70° C. until it is convenient to do so.

A sample of *E. coli* strain NEB 603 was deposited with the American Type Culture Collection (ATCC) on Jul. 3, 1990 and bears ATCC Accession No. 68354.

4.4 Properties of pMMhaeIIIRM 127-1: pMMhaeIIIRM 127-1 was isolated in *E. coli* ER1398 cells, all the HaeIII sites of which had been modified by the M.FnuDI MTase. The MTase was furnished by a second plasmid present in the cells, pMMfnuDIM 302:20-6.

We consider that the presence of pMMfnuDIM 302:20-6 was a crucial factor in enabling pMMhaeIIIRM 127-1 to be successfully isolated. We suspect that the haeIIIM gene is inadequately expressed in *E. coli*, and that, as a consequence, the DNA of the host fails to become fully protected from digestion by the R.HaeIII ENase. To remedy this problem, we augmented the amount of methylase in the cell by providing a second source, the cloned fnuDIM gene. The following observation supports our hypothesis that the fnuDIM gene is important in maintaining the viability of the HaeIII R-M clones:

When the plasmid DNA present in ER1398 [pMMhaeIIIRM 127-1, pMMfnuDIM 302:20-6] was purified, a mixture of both plasmids was obtained. (Plasmid pMMhaeIIIRM 127-1 is the predominant plasmid in the mixture since its copy number exceeds that of pMMfnuDIM 302:20-6.) The mixture was transformed into unmodified *E. coli* ER1398 cells, and most of the transformants recovered were found to have acquired only the pMMhaeIIIRM 127-1 plasmid; a minority of the transformants had acquired both plasmids. The former transformants were highly unstable; cultures of the transformants invariably became overgrown with cells that had lost the plasmid. It proved impossible to maintain the plasmid within cells for more than a few generations, nor even to grow a sufficiently large (500 ml) culture to enable plasmid preps to be made. On the other hand, the transformants in which both plasmids were present proved to be quite stable. No difficulty was experienced maintaining this strain, nor in growing large, homogeneous cultures. Evidently, on its own, the cloned HaeIII R-M system is unstable in *E. coli*. but it can be stabilized by addition of a supplementary methylase, in this case, the M.FnuDI methylase.

EXAMPLE 3

Purification of Recombinant FspI

*E. coli* strain NEB 588 ( *E. coli* RRI [pJBhhaIM 302-1, pMMfspIRM 119-1]), obtained above in Example 1, was grown in media consisting of 10 g/l tryptone, 5 g/l yeast extract, 5 g/l NaCl, polypropylene glycol 2000 0.1 ml/l, ampicillin 100 mg/l, chloramphenicol 200 mg/l (pH ad3usted to 7.2). The cells were grown at 37° C. with aeration and agitation. The cells were harvested at stationary phase by centrifugation and stored at −70° C..

50 grams of the frozen cell paste were thawed and suspended in 300 mls of buffer A (0.1M NaCl, 10 mM KPO₄ pH 7.4, 10 mM 2-mercaptoethanol, 0.1 mM EDTA). The remaining steps were performed at 40° C. The cell suspension was sonicated until 109 mg protein/g of cells was released. The supernatant was prepared by pelleting the debris in a refrigerated centrifuge for 50 minutes. The supernatant was adjusted to 0.3M NaCl.

The supernatant obtained (300 mls) was loaded on to a DEAE Sepharose column (5 cm×13.5 cm) which had been equilibrated in 0.3M NaCl A buffer. The enzyme was eluted with 350 mls of 0.3M NaCl buffer A. The entire eluate, 650 mls, was collected and diluted to 0.1M NaCl by addition of buffer A.

This enzyme solution was then applied to a Whatman P11 phosphocellulose column (5 cm×7 cm) which had been equilibrated in 0.1M NaCl, 10 mM KPo₄ pH 7.2, 10 mM 2-mecaptoethanol, 0.1 mM EDTA. The column was then washed with the equilibration buffer. A 1200 ml linear gradient was formed from 0.1 to 1.1M NaCl in equilibration buffer and applied to the column. Approximately 20 ml fractions were collected and assayed for FspI activity, as described above in Example 1, step 4.3. The FspI activity eluted at approximately 0.3M NaCl. The fractions with FspI activity were pooled (250 ml).

The pooled activity was then applied to an hydroxylapatite column (2.5cm×10 cm) which had been equilibrated in 0.1M NaCl buffer A. The column was then washed With 100 mls of 0.1M NaCl buffer A. A 400 ml linear gradient from 10 mM $KPO_4$ to 500 mM $KPO_4$ was formed and applied to the column. Approximately 5 ml fractions were collected and assayed for FspI activity, as described above in Example 1, step 4.3. Activity was detected in both the flow through (100 ml) and in fractions (13-27). The flow through and the active fractions were pooled (175 ml).

The pooled fractions were applied to a heparin-Sepharose column (1.5 cm×15 cm) which had been equilibrated in 0.1M NaCl buffer A. The column was washed with 60 ml of 0.1M NaCl buffer A. A 300 ml linear gradient from 100 mM to 1000 mM NaCl was formed and applied to the column. Approximately 5 ml fraction were collected and assayed for FspI activity, as described above in Example 1, step 4.3. The active fractions were pooled (60 ml) and dialyzed against 2 liters of buffer B (20 mM Tris-HCL pH 7.5, 10 mM 2-mercaptoethanol, 0.1M NaCl, 0.1 mM EDTA) for four hours. The dialysate was adjusted to the same conductivity of the dialyzing buffer by the addition of 10 mls of 20 mM Tris-HCL pH 7.5, 10 mM 2-mercaptoethanol, 0.1 mM EDTA.

The dialysate was applied to a HPLC MonoQ Column (1.0 ml bed volume, Pharmacia). The column was equilibrated in buffer B and a linear NaCl gradient from 0.1M to 0.6M NaCl (40 mls) was applied to the column. One ml fractions were collected and assayed for Fsp I activity, as described above in Example 1, step 4.3. The FspI activity eluted at 0.2M NaCl (fractions 13-23) and were pooled.

The pooled fractions were applied to a Sephadex G75 column (2.5 cm×97 cm, Pharmacia). The FspI was eluted with 10 mM $KPo_4$ pH 7.4, 0.3M NaCl, 10 mM 2-mercaptoethanol, 0.1 mM EDTA. The flow rate of the column was adjusted to about 0.2 ml per minute. Four ml fractions were collected. The fractions were assayed for FspI activity. Fractions 45-55 contained the FspI endonuclease and were pooled (43 ml). Bovine serum albumin was added to the pool at 50 ug/ml. The pool was then dialyzed against 50 mM KCl, 50% glycerol, 10 mM Tric-HCL pH 7.5, 1 mM DTT, 0.1 mM EDTA. The FspI preparation was then stored at −20° C.

The FspI endonuclease obtained was free of FspII and other non-specific endonucleases as determined by DNA digestion and agarose gel electrophoresis. Incubation of 50 units of FspI in 50 mM Potassium acetatem 20 mM Tris acetate, 10 mM magnesium acetate, 1 mM DTT (ph7.9) with 1 ug lambda DNA in a 50 ul volume at 37° C. for 16 hours produced the same agarose gel baning pattern as a one unit digest for one hour.

The FspI obtained was also free of exonuclease activity as determined by incubation of 50 units of Fsp I in 50 mM Potassium acetate, 20 mM Tris acetate, 10 mM magnesium acetate, 1 mM DTT (pH 7.9) with 1 ug of sonicated tritium labelled DNA in a 50 ul volume at 37° C. released only 0.02% of the tritium label as TCA soluble.

EXAMPLE 4

Purification of Recombinant HaeIII

*E. coli* strain NEB 603 (ATCC No. 68354)(*E. coli* ER 1398 [pMMhaeIIIRM 127-1, pMMfnuDIM 302:20-6]), obtained above in Example 2, was grown in media consisting of 10 g/l tryptone, 5 g/l yeast extract, 5 g/l NaCl, polypropylene glycol 2000 0.1 ml/l, ampicillin 100 mg/l, chloramphenicol 200 mg/l (pH adjusted to 7.2). The cells were grown at 37° C. with aeration and agitation. The cells were harvested at stationary phase by centrifugation and stored at −70° C.

210 grams of cell paste were thawed and suspended in 880 mls of A buffer (0.05M KCl, 20 mM $KPO_4$ pH 7.0, 10 mM 2-mercaptoethanol, 0.1 mM EDTA, 5% glycerol). The remaining steps are performed at about 4° C. The cell suspension was passed through a French Press (2X @12,000 PSIG) until 100 mg protein/gram of cells was released. The supernatant was prepared by pelleting the debris in a refrigerated centrifuge for 90 minutes. The supernatant was adjusted to 0.15M KCl.

The supernatant fluid (900 ml) was loaded on to a DEAE Seharose (Pharmacia) column (5.0 cm by 11.5 cm) which had been equilibrated in 0.15M KCl A buffer. The enzyme was eluted with 350 ml of 0.15M KCl A buffer. The entire eluate (1250 ml) was collected and adjusted to a final protein concentration of 7.0 mg/ml by the addition of A buffer.

This enzyme solution was then applied to a Whatman P11 phosphocellulose column (4 cm by 11 cm) which had been equilibrated to 0.15M KCl A buffer. The column was then washed with 200 ml equilibration buffer. A 1000 ml linear gradient from 0.15 to 1.2M KCl in A buffer was formed and applied to the column. Fractions of approximately 10 ml were collected and assayed for HaeIII activity, as described above in Example 2, step 4.3. The HaeIII activity eluted at approximately 0.7M KCl. The active fractions (45-70) were pooled (260 ml) and dialized against 2 liters A buffer for 16 hours in order to adjust the KCl concentration of the pool to 0.1M.

The dialysate was applied to a Heparin Sepharose (Pharmacia) column (4 cm by 7 cm) which had been equilibrated in 0.1M KCl A buffer. The column was then washed with 100 ml equilibration buffer. A 600 ml linear gradient from 0.1 to 1.0M KCl in A buffer was formed and applied to the column. Fractions of approximately 12 ml were collected and assayed for HaeIII activity, as described above in Example 2, step 4.3. The Hae III activity eluted at approximately 0.6M KCl. The active fractions (30-44) were pooled (180 ml).

The pooled fractions were applied to an Hydroxylapatite (Calbiochem) column (4 cm by 8 cm) which had been equilibrated in 0.6M KCl A buffer. The column was washed with 200 ml equilibration buffer. A 600 ml linear gradient from 20 mM $KPO_4$ to 500 mM $KPO_4$ in 0.6M KCl A buffer was formed and applied to the column. Fractions of approximately 10 ml were collected and assayed for HaeIII activity, as described above in Example 2, step 4.3. The enzyme eluted at approximately 0.2M $KPO_4$ and the active fractions (25-35) were pooled (110 ml). Bovine serum albumin was added to the pool to a final concentration of 65 ug/ml. The pool was then dialyzed against 2 liters of 50 mM KCl, 20 mM Tris-HCl pH 7.5, 1 mM DTT, 0.1 mM EDTA and 50% glycerol. The HaeIII preparation was then stored at −20° C.

The HaeIII endonuclease obtained was free of Hae II and other non-specific endonucleases as determined by DNA digestion and agarose gel electrophoresis. Incubation of 500 units of HaeIII in 50 mM Potassium acetate, 20 mM Tris acetate pH 7.9 10 mM Magnesium acetate, 1 mM DTT with 1 ug lambda DNA in a 50 ul volume at 37° C. for 16 hours produced the same agarose gel banding pattern as a one unit digest for one hour.

The HaeIII obtained was also free of exonuclease activity as determined by incubation for 4 hours of 250 units of Hae III in 50 mM Potassium acetate, 20 mM tris acetate, 10 mM magnesium acetate, 1 mM DTT (pH 7.9) with 1 ug of sonicated tritium labelled DNA in a 50 ul volume at 37° C. released only 0.2% of the tritium label as TCA soluble.

What is claimed is:

1. A method of cloning a restriction endonuclease gene encoding an R.FspI endonuclease comprising the following steps:
   (a) purifying DNA from a source containing the R.FspI restriction endonuclease to be cloned;
   (b) treating the purified DNA to form DNA fragments;
   (c) ligating the fragments into a cloning vector;
   (d) constructing a recipient cloning host, the DNA of which is protectively-modified against digestion by the restriction endonuclease due to the presence of a heterospecific methyltransferase;
   (e) introducing the ligated DNA into the protectively-modified host;
   (f) screening the clones to identify those that have acquired the gene coding for the R.FspI restriction endonuclease; and
   (g) isolating the close so-identified.

2. The method of claim 1, wherein the R.FspI restriction endonuclease is obtainable from Fisherella sp. ATTC No. 29114.

3. The method of claim 1, wherein protective-modification of the host is accomplished by cloning a gene coding for an M.HhaI modification methyltransferase into the host.

4. The method of claim 3, wherein the gene for the M.HhaI modification methyltransferase is obtainable from *Haemophilus haemolyticus* ATTC No. 10014.

5. An isolated DNA fragment comprising a nucleotide sequence which encodes the FspI restriction endonuclease produced by Fisherella species, ATTC No. 29114.

6. The DNA fragment of claim 5, further comprising a nucleotide sequence which encodes the FspI methylase produced by Fisherella species, ATTC No. 29114.

7. The DNA fragment of claim 5 or 6, wherein the DNA fragment is obtainable from the plasmid pMMfspIRM 119-1.

8. A cloning vector which includes the DNA fragment of claim 5 or 6.

9. A transformed host containing the vector of claim 8.

10. A method of producing substantially pure recombinant FspI restriction endonuclease comprising culturing a host cell transformed with the vector of claim 8 under conditions suitable for expression of FspI.

11. A method of producing an R.FspI restriction endonuclease comprising the following steps:
   (a) purifying DNA from a source containing the R.FspI restriction endonuclease to be cloned;
   (b) treating the purified DNA to form DNA fragments;
   (c) ligating the fragments into a cloning vector;
   (d) constructing a recipient cloning host, the DNA of which is protectively-modified against digestion by the restriction endonuclease due to the presence of a heterospecific methyltransferase;
   (e) introducing the ligated DNA into the protectively-modified host;
   (f) screening the clones and isolating those which contain the restriction endonuclease gene;
   (g) culturing the cells containing the clones of step f; and
   (h) recovering the R.FspI restriction endonuclease from the culture.

* * * * *